United States Patent [19]

Chen et al.

[11] Patent Number: 5,543,451

[45] Date of Patent: * Aug. 6, 1996

[54] POLYOLEFINS/ALKENYLLACTAMIDE COMPOSITION

[75] Inventors: Bing-Lin Chen, Germantown; James A. Barker, Memphis, both of Tenn.

[73] Assignee: Witco Corporation, Greenwich, Conn.

[*] Notice: The portion of the term of this patent subsequent to Apr. 27, 2010, has been disclaimed.

[21] Appl. No.: 493,490

[22] Filed: Jun. 22, 1995

Related U.S. Application Data

[60] Continuation of Ser. No. 5,585, Jan. 19, 1993, abandoned, which is a division of Ser. No. 791,562, Nov. 19, 1991, Pat. No. 5,206,273.

[51] Int. Cl.⁶ .................................. C08J 3/28; C08K 5/20
[52] U.S. Cl. .................................... 524/224; 523/300
[58] Field of Search ............................... 523/300; 524/224

[56] References Cited

U.S. PATENT DOCUMENTS 5,206,273 4/1993 Chen et al. ............................ 523/300

*Primary Examiner*—Peter D. Mulcahy
*Attorney, Agent, or Firm*—Lockwood, Alex, Fitzgibbon & Cummings

[57] ABSTRACT

A method for increasing the slip of polyolefins and improving the adhesion of water based inks of polyolefins by incorporating into the polyolefin an effective amount of a lactamide having the formula:

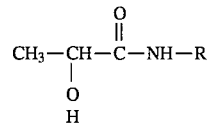

wherein R is alkenyl having from about 12 to about 22 carbon atoms. Optionally, there can be included with the lactamide a finely divided inorganic material. Also disclosed are compositions of matter comprising a polyolefin, such as homopolymers and copolymers of ethylene and propylene, the aforedescribed lactamide and optionally a finely divided inorganic material. Also described is the new compound, N-erucyl lactamide.

5 Claims, No Drawings

POLYOLEFINS/ALKENYLLACTAMIDE COMPOSITION

This a continuation of application Ser. No. 08/005,585 abandoned, filed Jan. 19, 1993 which is a division of Ser. No. 07/791,562 filed Nov. 12, 1991 U.S. Pat. No. 5,206,273 abandoned.

BACKGROUND

This invention relates to polyolefinic polymers having improved properties. In particular this invention relates to improving the slip and ink adhesion of polyolefinic compositions. An important aspect of this invention is a polyolefinic composition containing an N-substituted lactamide and having improved adhesion to water-based ink.

Olefin homopolymers and copolymers are of commercial importance for the manufacture of numerous articles such as films and other items. In order to be useful for many of these functions it is desirable that the polyolefinic composition have good slip characteristics. This can be determined by measuring the coefficient of friction of the polyolefin. It is also important that the polyolefinic composition have good printability and adhesion to Water-based inks, as these become more widely used in industries that engage in printing on them.

In order to obtain a satisfactorily low coefficient of friction, often slip agents are added to the polyolefin to lower its coefficient of friction below about 0.5, preferably below 0.3. Many slip agents and other additives for polyolefins are disclosed in the literature. These additives will lower the coefficient of friction of the polyolefin to desired levels, permitting ready handling of shaped articles and films prepared from the polyolefinic material. Polyolefinic polymers having poor slip characteristics are difficult to handle when the polymer is manufactured in the customary manner of large rolls. During storage and subsequent processing, the low slip films tend to adhere layer to layer or block together. Also such films can encounter large frictional forces in processing equipment that often cause distortions and even tearing of the film, especially when using thin film.

Haeske et al U.S. Pat. No. 3,266,924 discloses the blending of a mixture of finely divided siliceous material and a fatty acid amide slip agent into polyethylene to enhance its slip and blocking properties. Ross et al U.S. Pat. No. 3,326,840 discloses the incorporation of a small amount of a mono-N-substituted saturated carboxylic acid amide of the formula:

wherein R is an aliphatic acyl radical having from 12 to 30 carbon atoms and R' is an aliphatic group having from 1 to 6 carbon atoms, especially an alkylol group, into a copolymer of ethylene and an aliphatic ethylenically unsaturated carboxylic ester to improve its resistance to blocking and improve its slip properties.

Foster U.S. Pat. No. 3,647,738 discloses blending an amide having the formula:

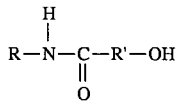

wherein R is an alkenyl radical having 18 to about 22 carbon atoms and R' is a divalent hydrocarbon radical containing 3 to 15 carbon atoms with an alpha-olefin polymer composition to provide compositions having low blocking and no bloom characteristics and high slip properties.

While the foregoing patents and other literature disclose a variety of additives that improve the slip and/or blocking properties of polyolefins, it is also necessary that the polyolefinic compositions containing the slip agents have excellent ink adhesion, particularly to water based inks and printability so that the molded article, film or other item made from the polymer can be suitably printed. Of late it has become highly desirable for environmental reasons, such as to reduce emissions of volatile organic compounds, that the inks used to print on the polyethylene composition be water-based inks.

Accordingly it is an object of the present invention to improve the slip properties of polyolefins.

Still another object of the present invention is to improve the adhesion of water based inks to polyolefins.

still another object of the present invention is to improve the ink adhesion of water-based inks to polyolefins containing materials for improving the slip properties of the polyolefins.

Also an object of the present invention is the prevention of polyolefin films from adhering to each other during storage.

Another object of the present invention is to impart the desired slip, printability and adhesion to water-based inks to polyolefin compositions without adversely affecting the optical properties of the polyolefin.

Other objects of the present invention will become apparent from the ensuing description.

SUMMARY OF THE INVENTION

The compositions of this invention having improved slip and adhesion of water based inks comprise a polyolefin polymer and an effective amount of a lactic acid amide having the structural formula:

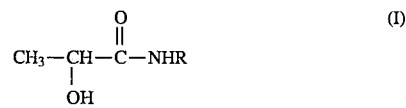

wherein R is alkenyl having from about 12 to about 22 carbon atoms, and optionally an effective amount of a finely divided inorganic material. The method of the present invention comprises incorporating an effective amount of a lactic acid amide of the above structural formula and optionally an effective amount of a finely divided inorganic material into a polyolefin polymer forming a polyolefin composition having a lower coefficient of friction, excellent printability and good adhesion of inks, particularly water-based inks.

DETAILED DESCRIPTION OF THE INVENTION

The present invention provides for polyolefins having improved slip properties, as evidenced by their lower coefficient of friction and improved adhesion to inks, particularly water-based inks. The polyolefins can be homopolymers and copolymers and mixtures thereof.

Among the polyolefins of this description are ethylene and propylene homopolymers and copolymers. Polyethylene can be low density and high density polymeric material. Linear low density polyethylene is in general a copolymer of ethylene and up to about 10 weight percent of a second olefin, such as propylene, butene, hexene or octene. High density polyethylene is normally a homopolymer.

There are, basically, two types of olefin polymerization techniques for preparing high molecular weight olefin polymers and copolymers. The oldest commercial technique involves high pressure, high temperature, and the use of a free radical initiator, such as a peroxide; these type polymers are generally known as low density polyethylene (LDPE). These LDPE polymers contain branched chains of polymerized monomer units pendant from the main polymer "backbone" and generally have densities in the range of about 0.910–0.935 gms/cc.

The other commercially-used technique involves coordination catalysts of the "Ziegler" type or "Phillips" type and includes variations of the Ziegler type, such as the Natta type. These catalysts may be used at very high pressures, but are generally used at very low or intermediate pressures. The products made by these coordination catalysts are generally known as "linear" polymers because of the substantial absence of branched chains of polymerized monomer units pendant from the main polymer "backbone," and they are also generally known as high density polyethylene (HDPE). Linear polyethylene (HDPE) ordinarily has a density in the range of 0.941 to 0.965 gms/cc.

Also used in the present invention are "linear" type ethylene polymers wherein ethylene has been polymerized along with minor amounts of alpha, beta, ethylenically unsaturated alkenes having from 3 to 12 carbons per alkene molecule, preferably 4 to 8. The amount of the alkene comonomer is generally sufficient to cause the density of the polymer to be substantially in the same density range as LDPE, due to the alkyl side chains on the polymer molecule, yet the polymer remains in the "linear" classification; they are conveniently referred to as "linear low density polyethylene" (LLDPE). These polymers retain much of the strength, crystallinity, and toughness normally found in HDPE homopolymers of ethylene, but the highest alkene comonomers impart high "block" characteristics to extrusion-cast films and the high "slip" (i.e. low coefficient of friction) characteristic inherently found in HDPE is diminished.

Other homopolymers which can be use include: polypropylene, polybutene-1, poly(4-methylpentene-1) and the like.

Exemplary of the copolymers of olefinically unsaturated aliphatic hydrocarbons which are preferred are ethylenepropylene copolymers, containing about 1 to about 99% by weight, based on the total copolymer, of propylene copolymerized therein, ethylene-butene-1 copolymers containing about 1 to about 99%, based on the total copolymer of butene-1 copolymerized herein ethylene-hexene-1 copolymers containing about 1 to about 99% by weight based on the total copolymer of hexene-1 copolymerized therein and the like.

The homopolymers and copolymers of olefinically unsaturated aliphatic hydrocarbons referred to above can be made by either free radical catalyzed high pressure techniques or anionic catalyzed low pressure techniques known in the art and described in "Crystalline Olefin Polymers" Part I by R. A. V. Raff and K. W. Doak, Interscience Publishers, New York City 1965 which is incorporated herein by reference.

The ethylene-acrylic acid interpolymers ethylenemethacrylic acid interpolymers, ethylene-vinyl acetate interpolymers and ethylene-alkyl acrylate methacrylate interpolymers of this invention can be made by the free radical, random interpolymerization of ethylene with the corresponding comonomer using methods well known in the art including bulk, solution, aqueous suspension, non-aqueous dispersion and emulsion techniques in either batch or continuous process.

The melt index of the ethylene/vinyl acetate copolymers of this invention can range from about 0.01 to 500 dg/min. with a range of about 0.2 to 20 dg/min being preferred. These ethylene-vinyl acetate copolymers preferably contain about 1.5 to about 20% by weight of vinyl acetate copolymerized therein.

There are numerous polyolefin resins useful in the present invention. For example, Rexene high molecular weight, low density polyethylene resins made by the polymerization of ethylene using a free radical initiator at high pressure and high temperature was used in the experimental work reported in Examples 2–11. These polyethylene resins have the following properties:

Density 9.921 grams/cc

Melt Index 1.0 grams/10 minutes

Tensile (yield) 1500 psi

Tensile (at break) 2100 psi

Ultimate Elongation 500%

Secant Modulus 50,000 psi

Hardness 48 Shore D

Softening Point (Vicant) 200° F.

Among other polyolefins useful in the present invention are high molecular weight, high density polyethylene resins such as Paxon 4100 of Allied Chemical Company which has a density of 0.950 grams/cc and a melt index 0.5 grams/10 minutes; linear low density polyethylene resins such as Dowlex 4047 of Dow Chemical Co. which has a density of 0.917 grams/cc and a melt index of 2.3 grams/10 minutes; polypropylene, such as Petrothene PP 8000-GK of Quantum Chemical Co. which has a density between about 0.89–0.91 grams/cc and a melt index of 5.0 grams/10 minutes and ethylene-vinyl acetate copolymer resins such as Rexene PE 1335 which has a density of 0.924 grams/cc; a melt index of 2.0 grams/cc, and a vinyl acetate content of 3.3%. These materials are merely representative of polyolefins useful in the present invention which are numerous and can be selected depending upon the desired properties of the final composition.

Various additives are often incorporated into the polyolefin. One such group of additives are antioxidants such as hindered phenols, phenolic phosphites, secondary arylamines and the like. These antioxidants are used in quantities between about 0.01 to about 1 weight percent of the polymer. Other additives such as colorants, antiblocking agents, antistatic agents and lubricants are commonly used. Also lubricants are often incorporated into polyolefin compositions, particularly polypropylene and high density polyethylene in order to improve the processability of the polymer.

The polyolefin compositions of the present invention comprise polyolefin polymer and an effective amount of the aforedescribed lactic acid amide and optionally an effective amount of a finely divided inorganic material sufficient to improve the slip properties of the polyolefin and also improve the adhesion of water-based inks, thereto.

Slip is the ability of films of the polyolefins to slide past one another. Antiblocking is the ability of films of the polyolefins to avoid adhering to one another and to separate from one another. Printability is the ability for the films to be printed. Adhesion is retention of the ink on the film.

As previously indicated, there are many materials known to improve slip and blocking properties of films. Since environmental concerns have arisen as to organic solvents, it has become desirable to use water-based inks. The solvent-based inks previously used are often considered to be environmentally undesirable. The materials previously used as slip and antiblocking agents such as unsubstituted amides of long-chain fatty acids, particularly erucamide, do not provide the polyolefinic polymer with the desired adhesion to water-based inks. This property is provided by the present compositions and method.

In general the composition and methods of the present invention require that the polyolefin contain an effective amount of the N-alkenyl lactamide of structural Formula I. This amount will vary depending on several variables, particularly the particular polyolefin and the selection of the N-alkenyl lactamide. Certain of the N-alkenyl lactamides are more effective in the polyolefins and thus lower concentrations can be used in the polymer to obtain the desired properties. It has also been found that certain of the N-alkenyl lactamides when used in higher concentrations than necessary to obtain improved slip and adhesion to water-based inks will be ineffective in certain polyolefins. Thus, for example, N-erucyl lactamide can be used effectively in polyolefins composition in amounts between about 0.05 and 0.3 weight percent of the polyolefin, although other amounts may be useful in specific compositions. On the other hand, the amount of N-oleyl lactamide that is useful in the present compositions and methods is between about 0.1 and about 0.25 weight percent of the polyolefin. Thus, the exact concentrations of the N-alkenyl lactamide used in the present compositions and methods will depend on various factors.

Included among the lactic acid amide compounds useful in the present invention are N-erucyl lactamide and N-oleyl lactamide.

Optionally, the compositions of the present invention may contain components in addition to the lactamides which further the improvement of the slip properties and adhesion of the water-based ink of the polyolefin polymer. For example, it has been found that the addition of a finely divided inorganic material can enhance the slip and adhesion to water-based inks of the polyolefin compositions of the present invention. Thus the coefficient of friction of the polyolefin which is lowered by the addition of an effective amount of a lactic acid amide in accordance with the present invention, can often be lowered further by the presence of an effective amount of finely divided inorganic material. In general the presence of from about 0.05 to about 1.0, preferably from about 0.1 to about 0.5, weight percent of the finely divided inorganic material in the polyolefin composition will be of value in lowering the coefficient of friction and improving the water based ink adhesion of the polyolefin polymers. Examples of these finely divided materials are silica, mica, talc, diatomaceous earth and calcium carbonate.

The polyolefin composition of the present invention can be prepared by admixing the polyolefin polymer, the lactic acid amide and the finely divided inorganic material, if one is used, by various methods.

One method of preparation is to blend a masterbatch of the polyolefin polymer containing the lactic acid amide and other additives. This can be accomplished by grinding polyolefin pellets in a mill to form a coarse granule. The lactic acid amide and other additives are melted onto the surface of the polyolefin granules with the use of a heat lamp. Then the granules are mixed and the mixture is extruded through a capillary die to form a strand which is pelletized. If desired, the pelletizing procedure can be repeated as many times as desired so as to insure adequate mixing of the components.

The masterbatch can then be added to virgin polyolefin polymer by shaking and tumbling the masterbatch and polyolefin pellets. Then the mixture can be converted into the desired product by extrusion, blow molding, blow extrusion, compression molding or other commercial method.

When an extrusion is desired, the mixture can be extruded through a two-stage mixing screw with a 3:1 compression ratio and a 20:1 length:diameter ratio, although other equipment can be used. The temperature of the barrel and die are controlled. As the molten plastic tube emerges from the die it can be blown with air to the predetermined diameter and cooled with air.

Also the composition of the present invention can be cast into film by extrusion through a slot die using a simple screw extruder having characteristics such as those for the afore-described two-stage mixing screw. Similar test results are obtained from cast film as with blown films. Following are the procedures used for testing polyolefin compositions containing lactic acid amides in accordance with the present invention.

Compression molded plaque product can be made by placing low density polyethylene pellets containing the desired additives in a metal mold. In the following examples a mold containing the polyolefin pellets (25 grams) was placed in a Dake Hydraulic Laboratory Press (Model 44425, 25 ton capacity, 9 inch×9 inch platen size) at 450° F. and held at 25 thousand pounds hydraulic pressure for 3.5 minutes. After cooling and release of the pressure, the molded plaque was removed from the mold and tested both for slip and for adhesion to a water-based ink.

When the additives of the present invention are used at effective levels, improvements in printability and ink-adhesion are seen. In the absence of a suitable ASTM test for measuring printability and ink-adhesion properties, the following printability test was devised. Samples of polyolefin films (10"×5") are corona treated in two paths for a total of 50 seconds using a High Frequency Corona Treater equipped with a 2-⅝" field effect electrode, Model BD-20C, made by Electro-Technic Products, Inc. The field effect electrode is held at about 1.5 cm from the film surface during corona treatment. Printability testing is done on the film one week after the corona treatment. A 10"×2-¾" print stripe is made on the film with a water-based ink, Hydropoly Red ink, S89–4710B, from Sun Chemical Co., using a spring-loaded handproofer having 2-¾ inch printing width. The printed film is dried in an oven at 160° F. for 20 seconds. The appearance of the print is rated good (G), fair (F), or poor (P), with respect to the smoothness of ink coverage and the presence of visible pinholes.

Ink adhesion is evaluated by hand-pulling a piece of Scotch 600 tape off the printed surface to determine the amount of ink which stays on the surface. A scale of 0 to 10 was used with 0 representing 0 ink adhesion and 10 representing 100% of ink adhered to the printed surface. Two replicates were used, with the average value reported.

The coefficient of friction was determined by ASTM D1894–75, moving sled/stationery plane test method, using an Instron 1130 Universal Testing Instrument. Slip measurements were made one week after extrusion on five different film segments and the average reported. A coefficient of friction of >0.5 is considered poor; 0.30 to 0.5 — fair and <0.30 — desirable.

Example 1 describes the preparation of N-erucyl lactamide.

EXAMPLE 1

Preparation of N-Erucyl Lactamide

A one-liter, 3-neck flask equipped with a stirrer, thermometer, Dean-Stark receiver and condenser was charged with erucyl amine (320 grams; 1.0 mol), and ethyl lactate (130 grams; 1.1 mol) and stirred at 130° C. for 8 hours under a nitrogen atmosphere. The reaction was followed by total amine value and infrared spectrum analyses. The reaction mixture was then stripped at 135° C., 30 mmHg vacuum for 30 minutes to afford 368 g (94% yield) of N-erucyl lactamide. This product had a total amine value of 1.6; a hydroxy value of 139.8 and a melting point of 50° C. The structure of this product was confirmed by infrared analysis showing disappearance of the absorption band at about 5.7 microns for ethyl lactate and the presence of a strong amide absorption band at about 6.15 microns, along with hydroxy absorption band at about 2.0 to 3.1 microns.

The following examples were performed with various polyolefinic compositions containing the lactic acid amides of the present invention and with a control containing no additive. The previously discussed procedures were used to evaluate the slip properties, the printability and adhesion of water-based inks to the test compositions.

EXAMPLE 2

N-erucyl lactamide was incorporated into low density polyethylene resin. Then the resulting compositions were extrusion blown to form films. The low density polyethylene resin was Rexene high molecular weight, low density polyethylene resin previously described. The coefficient of friction (C.O.F.), printability and adhesion to water-based inks of each composition were determined by the previously discussed procedures. Also a composition comprising the low density polyethylene without a slip agent additive and compositions containing the slip agent in combination with Microken 801 diatomaceous earth were tested, with the following results:

| N-Erucyl Lactamide (ppm) | Microken 801 (ppm) | C.O.F. | Ink Adhesion | Printability |
|---|---|---|---|---|
| 500 | 0 | 0.74 | 9.5 | G |
| 500 | 1500 | 0.39 | 10.0 | G |
| 1000 | 0 | 0.37 | 9.2 | G |
| 1000 | 1500 | 0.23 | 10.0 | G |
| 2000 | 0 | 0.23 | 8.0 | G |
| 2000 | 1500 | 0.18 | 9.0 | G |
| 3000 | 0 | 0.15 | 1.2 | G |
| 3000 | 1500 | 0.14 | 3.5 | G |
| 3000 | 3000 | 0.14 | 4.6 | G |

EXAMPLE 3

The procedures of Example 2 were repeated with low density polyethylene resin compositions containing N-erucyl lactamide (2000 ppm) and various finely divided inorganic materials, as follows:

| Calcium Carbonate | Microken 801 | Mica | Silica | Talc | C.O.F. | Ink Adhesion | Printability |
|---|---|---|---|---|---|---|---|
| 1500 | 0 | 0 | 0 | 0 | 0.19 | 8.0 | G |
| 0 | 1500 | 0 | 0 | 0 | 0.20 | 9.0 | G |
| 0 | 0 | 1500 | 0 | 0 | 0.24 | 6.0 | G |
| 0 | 0 | 0 | 1500 | 0 | 0.16 | 5.0 | G |
| 0 | 0 | 0 | 0 | 1500 | 0.18 | 4.0 | G |

EXAMPLE 4

The procedures of Example 2 were repeated with low density polyethylene resin compositions containing several combinations of N-oleyl lactamide and Microken 801 diatomaceous earth, as follows:

| N-Oleyl Lactamide (ppm) | Microken 801 (ppm) | C.O.F. | Ink Adhesion | Printability |
|---|---|---|---|---|
| 500 | 0 | 0.73 | 9.5 | G |
| 500 | 1500 | 0.65 | 9.5 | G |
| 1000 | 0 | 0.63 | 8.0 | G |
| 1000 | 1500 | 0.37 | 9.0 | G |
| 2000 | 0 | 0.56 | 3.0 | F |
| 2000 | 1500 | 0.26 | 7.0 | G |
| 3000 | 0 | >1 | 0.7 | P |
| 3000 | 1500 | 0.31 | 3.5 | P |
| 0 | 0 | 0.95 | 10 | G |

EXAMPLE 5

The procedure of Example 2 were repeated with ethylene-vinyl acetate copolymer resin compositions containing erucamide, a commercial slip agent, N-erucyl lactamide and Microken 801 diatomaceous earth, with results as follows:

| Erucamide (ppm) | N-Erucyl Lactamide (ppm) | Microken 801 (ppm) | C.O.F. | Ink Adhesion | Printability |
|---|---|---|---|---|---|
| 0 | 0 | 0 | >1.0 | 9.7 | G |
| 2000 | 0 | 0 | >1.0 | 0 | G |
| 2000 | 0 | 3000 | 0.12 | 0 | G |
| 0 | 2000 | 0 | >1.0 | 9.0 | G |
| 0 | 2000 | 3000 | 0.18 | 7.7 | G |
| 0 | 1000 | 3000 | 0.33 | 9.5 | G |

EXAMPLE 6

Example 2 was repeated with low density polyethylene (LDPE), linear low density polyethylene (LLDPE), high density polyethylene (HDPE) and polypropylene (PP) as the polyolefins, and N-erucyl lactamide and Microken 801 diatomaceous earth as additives, with results as follows:

| Polyolefin | N-Erucyl Lactamide (ppm) | Microken 801 (ppm) | C.O.F. | Ink Adhesion | Printability |
|---|---|---|---|---|---|
| LDPE | 0 | 0 | 0.95 | 10.0 | G |
| LDPE | 2000 | 3000 | 0.17 | 8.1 | G |
| HDPE | 0 | 0 | 0.22 | 10.0 | G |
| HDPE | 2000 | 3000 | 0.23 | 10.0 | G |
| LLDPE | 0 | 0 | >1.0 | 9.0 | G |
| LLDPE | 1000 | 3000 | 0.26 | 5.5 | G |
| PP | 0 | 0 | 0.62 | 7.9 | G |
| PP | 2000 | 3000 | 0.46 | 6.3 | G |

EXAMPLE 7

Example 2 was repeated except that the polyolefin was extruded into cast polymer films with results as follows:

| Polyolefin | N-Erucyl Lactamide (ppm) | Microken 801 (ppm) | C.O.F. | Ink Adhesion | Print-ability |
|---|---|---|---|---|---|
| LDPE | 0 | 0 | 1.40 | 9.8 | G |
| LDPE | 2000 | 3000 | 0.19 | 9.0 | G |
| LLDPE | 0 | 0 | >1.0 | 9.7 | G |
| LLDPE | 2000 | 3000 | 0.18 | 2.2 | G |
| PP | 0 | 0 | 0.84 | 6.6 | G |
| PP | 2000 | 3000 | 0.31 | 6.0 | G |

EXAMPLE 8

Example 2 was repeated with low density polyethylene resin containing erucyl lactamide and Microken 801 diatomaceous earth compression molded into plaques, with the following results:

| Polyolefin | N-Erucyl Lactamide (ppm) | Microken 801 (ppm) | C.O.F. | Ink Adhesion | Print-ability |
|---|---|---|---|---|---|
| LDPE | 0 | 0 | 0.43 | 9.5 | G |
| LDPE | 2000 | 3000 | 0.11 | 6.0 | G |

EXAMPLE 9

Example 2 was repeated using Erucamide, a commercial slip agent, and N-ethanol stearamide as comparison for the N-erucyl lactamide of the present invention, with the following results:

| N-Erucyl Lactamide (ppm) | Erucamide (ppm) | N-Ethanol Stearamide (ppm) | Microken 801 (ppm) | C.O.F. | Ad-hesion |
|---|---|---|---|---|---|
| 0 | 0 | 0 | 0 | 0.95 | 10 |
| 0 | 0 | 0 | 1500 | 0.73 | 10 |
| 2000 | 0 | 0 | 0 | 0.23 | 8.0 |
| 2000 | 0 | 0 | 1500 | 0.18 | 9.0 |
| 0 | 2000 | 0 | 0 | 0.20 | 0 |
| 0 | 2000 | 0 | 1500 | 0.14 | 0 |
| | | 2000 | 0 | 0.64 | 2.9 |
| | | 2000 | 1500 | 0.39 | 1.0 |

EXAMPLE 10

The films prepared in Example 9 were then subjected to different corona treatment times after the preparation of the film. Ink adhesion of the water-based ink was made one week after the corona treatment with the following results. Prolonged corona treatment of films containing erucamide, the commercial slip agent, did not produce any meaningful improvement in ink adhesion. The compositions containing N-erucyl lactamide afforded very good ink adhesion upon prolonged corona treatment:

| Additive* | Corona Treatment Time (Sec.) | Ink Adhesion |
|---|---|---|
| Erucamide | 50 | 0 |
| | 100 | 0.5 |
| N-Erucyl lactamide | 50 | 9.0 |
| | 75 | 10.0 |

*0.2% by weight plus 0.15% Microken 801.

As can be seen from the results of the experimental data, the use of specific lactamides in polyolefins improves the slip of the polyolefins and also improves adhesion to water-based ink. Furthermore the lactamide can be used in combination with finely divided inorganic material. This combination of components enhances the increase in slip and ink adhesion of the polyolefinic compositions. These optional materials generally have a particle size of from 0.1 to about 100 microns, or higher. Included among the finely divided inorganic materials useful in combination with the lactamides in the present invention are silica, mica, talc, diatomaceous earth and calcium carbonate. The finely divided inorganic material is generally used in amounts of from about 0.05 to about 1.0, preferably from about 0.1 to about 0.5 weight percent of the weight of the polyolefin polymer.

A corona discharge is a treatment often used in this industry to improve the ink adhesion and printability of polymers. This treatment can also be used to enhance the properties of the polyolefin compositions containing the lactamide in accordance with this invention. Other like treatments can also be used with the methods and compositions of this invention. It should be noted that 50 seconds corona treatment is used in this invention to distinguish various additives. Prolonged corona treatment of polyolefins usually results in better ink-adhesion to water-based ink.

It should be understood that the embodiments of the present invention which have been described are merely illustrative of a few of the applications of the principles of the present invention. Numerous modifications ma be made by those skilled in the art without departing from the spirit and scope of the invention.

We claim:

1. A composition of matter comprising a polyolefin and 0.05 to 0.3 weight percent based on the weight of the polyolefin of at least one lactamide having the structural formula:

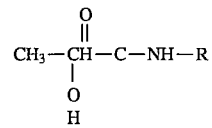

wherein R is alkenyl having from about 12 to about 22 carbon atoms.

2. The composition of matter of claim 1 wherein the polyolefin is a homopolymer or a copolymer of ethylene or a homopolymer or a copolymer of propylene.

3. The composition of matter of claim 2 wherein the polyolefin is a low density polyethylene resin.

4. The composition of matter of claim 2 wherein the lactamide is N-erucyl lactamide.

5. The composition of matter of claim 2 wherein the lactamide is N-oleyl lactamide.

* * * * *